United States Patent van der Maas et al.

[11] Patent Number: 5,889,197
[45] Date of Patent: Mar. 30, 1999

[54] GAS CHROMATOGRAPH APPARATUS

[75] Inventors: Martinus Frans van der Maas, Arnumuiden; Johannes Marinus Petrus van Deursen, Middelburg; Ewie de Kuyper, Cruquius, all of Netherlands

[73] Assignee: SGT Explotaitie B.V., Middleburg, Netherlands

[21] Appl. No.: 967,676

[22] Filed: Nov. 10, 1997

[30] Foreign Application Priority Data

Nov. 11, 1996 [NL] Netherlands ............................ 1004496

[51] Int. Cl.$^6$ ............................ G01M 30/04; B01D 53/02
[52] U.S. Cl. .................................. 73/23.42; 96/105; 95/82
[58] Field of Search ............................... 73/23.41, 23.42, 73/864.86; 96/105, 106; 95/89, 82

[56] References Cited

U.S. PATENT DOCUMENTS 4,890,502  1/1990  Elias et al. .
5,105,652  4/1992  Manfredi et al. .

FOREIGN PATENT DOCUMENTS 636 882 A1  2/1995  European Pat. Off. .
87 15 782   1/1988  Germany .
195 46 952  6/1996  Germany .
91/13349    9/1991  WIPO .

Primary Examiner—Herzon Williams
Assistant Examiner—Jay L. Politzer
Attorney, Agent, or Firm—Wiengarten, Schurgin, Gagnebin & Hayes LLP

[57] ABSTRACT

Device for connecting a first duct of a very small diameter, such as for instance a needle or a capillary column, to a second duct, wherein the device comprises a receiving part and a sealing element, wherein the receiving part is provided with a duct bore in which the first duct is slidably receivable, wherein the receiving part is also provided with a sealing-element bore which intersects the duct bore and in which the sealing element is slidably received, wherein the sealing element is provided with a recess, wherein the sealing element is adapted to assume a sealing position in which the duct bore is sealed, and is adapted to assume a connecting position in which the two duct bore parts on either side of the sealing-element bore are in fluid connection with each other via the recess, wherein the sealing element is biased in the sealing position by a spring under spring action.

16 Claims, 8 Drawing Sheets

View B-B

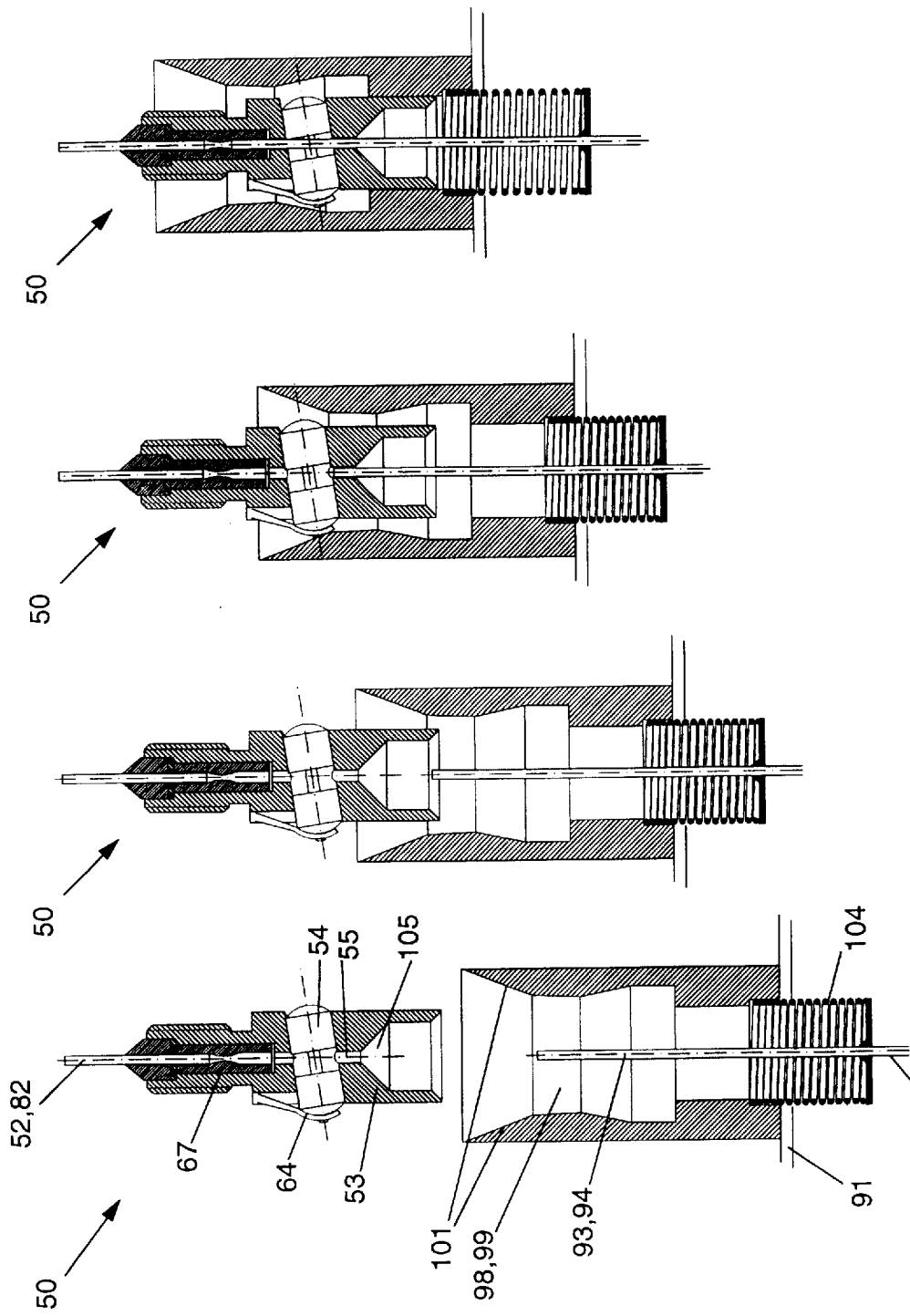

GAS CHROMATOGRAPH APPARATUS

Device for connecting a first duct of a very small diameter, such as for instance a needle or a capillary column, to a second duct, wherein the device comprises a receiving part and a sealing element, wherein the receiving part is provided with a duct bore in which the first duct is slidably receivable, wherein the receiving part is also provided with a sealing-element bore in which the sealing element is slidably received, wherein the sealing element is adapted to assume a sealing position in which the duct bore is sealed and is adapted to assume a connecting position in which the two duct bore parts on either side of the sealing-element bore are in fluid connection with each other, wherein the sealing element is biased in the sealing position by a spring under spring action.

The invention also relates to a coupling device for an injector and a detector of a gas chromatograph and to a cassette comprising a capillary gas chromatography column, which cassette is adapted to cooperate with the injector and the detector according to the invention. Further, the invention relates to an injector and a detector and to a gas chromatograph comprising such injector and/or detector.

The device described in the opening paragraph is known from German 'Gebrauchsmuster' DE-U-8715782, where it is used in the needle-insert part of an injector. In the known device, the main center line of the sealing element includes an acute angle with the center line of the duct bore. In the sealing position of the sealing element, an end face of the sealing element is located in the duct bore. This end face includes an angle with the duct bore. When a needle is inserted into the duct bore, it strikes the end face. When the needle is pushed through further, the sealing element is pressed, against the spring action, from the sealing position into the connecting position. The drawback of this construction is that it is necessary to bring the sealing element from the sealing position into the connecting position with the needle. In the case of a needle, this is still possible, however when a capillary tube made of, for instance, glass were inserted into the duct bore, the fee end of the capillary tube would almost certainly break under influence of the asymmetrical point load which the end face of the sealing element would exert on the end of the capillary tube. Hence, the device used in the known injector at the location of the needle-insert part is not suitable for applications where instead of a needle, a more fragile duct, such as for instance a capillary column, is to be connected to a second duct. Another drawback of the known device is that it involves the use of a sealing ring made of flexible material, which will generally be manufactured from plastic or rubber. Under influence of the relatively warm injector housing, such sealing ring may give off softeners or like substances, which may adversely affect the measurement to be carried out by the gas chromatograph.

Before proceeding to the solution to the abovementioned problems, a brief explanation will first be given of the background of the field of technology to which the present invention relates.

This concerns the field of technology of the gas chromatography. The known gas chromatograph comprises an oven with an injector and a detector, which injector and detector can be interconnected by means of a capillary gas chromatography column. The gas chromatography column comprises a capillary tube made of glass or like material, which tube is provided with a coating that reduces the tube's liability to breakage. Such gas chromatography columns should regularly be replaced, for instance because for measuring one substance a different column is used than for measuring another substance. Hence, replacing the columns is an operation which takes place regularly and which, in respect of the known apparatus, can only be performed by trained analysts. The known columns are connected to the outlet part of the injector and the inlet part of the detector by means of a clamp fitting. Such clamp fitting can be loosened by means of, for instance, an open-end spanner, whereafter the clamping becomes looser and the column can be pulled from the injector, respectively detector. As the clamp fitting is located in the oven space, it will have a high temperature, which complicates the loosening of the clamp fitting. Moreover, the feed end and the discharge end of the gas chromatography column should extend by a given length into the injector, respectively detector. Hence, the clamping of the column ends should be performed very accurately. If the feed end or the discharge end does not extend into the injector chamber, respectively detector chamber by the correct length, this may have a dramatic impact on the values measured. Another problem in respect of the injector of the known gas chromatograph concerns the needle-insert part of the injector. In the most usual gas chromatograph, the needle-insert part of the injector is provided with a so-called septum. This is a rubber or plastic plate of a slight thickness through which the needle is passed, by means of which needle the sample to be measured is introduced into the injector. The piercing of the septum, which is manufactured from rubber or plastic, does not exclude the danger of a rubber particle ending up in the injector chamber. As a fairly high temperature may prevail in the injector chamber, there is the chance that the rubber burns, causing the products of combustion to disturb the measuring values.

The drawbacks of the known needle-insert part are partly overcome by the needle-insert part described in the above-cited DE-U-8715782. However, that needle-insert part, too, entails drawbacks as explained hereinabove. It is clear that all these problems essentially result from the fact that connecting a first duct of a very small diameter, such as for instance a needle or a capillary gas chromatography column, to a second duct, such as for instance an injector chamber or a duct leading to a detection space, and clamping such first duct, is particularly troublesome.

The object of the invention is to adjust the device of the type mentioned in the opening paragraph in such a manner that not only a needle can thereby be connected to a second duct, but also less firm ducts of a very small diameter, such as for instance a capillary column made of glass or a very thin, fragile needle.

To this end, according to the invention, the device is characterized in that it comprises control means which engage the sealing element for bringing the sealing element from the sealing position into the connecting position, against the spring action.

Owing to the presence of the control means, the sealing element can be moved into the connecting position without the free end of the first duct having to be asymmetrically loaded for this purpose. In itself, the first ducts can take up a considerable pressure in the direction of the main center line thereof. Precisely when the first ducts are loaded obliquely, as is the case in the above-cited German 'Gebrauchsmuster', damage to the first duct is caused very quickly.

With the device according to the invention, the first duct can be connected to the second duct in a very simple manner by pushing the sealing element temporarily into the connecting position by means of the control means, after which the first duct can be passed through the duct bore, after which the sealing element can be released and comes to abut against the first duct under influence of the spring action. Due to the spring action, the sealing element will clamp the first duct in the duct bore so that a connection is established.

According to a further elaboration of the invention, the sealing element comprises two opposite end faces, with the control means being designed as a guide section engaging at least one of the end faces of the sealing element. When the first duct is being inserted, the guide section is moved along the end face of the sealing element, so that the sealing element at least temporarily assumes the connecting position, enabling the first duct to be passed through the duct bore.

In an alternative further elaboration of the invention, the sealing element comprises two opposite end faces, with the control means being designed as a leaf-spring element comprising a lever by means of which the position of the leaf spring and, accordingly, the position of the sealing element is adjustable.

In this alternative embodiment, the sealing element can, through operation of the lever, be brought from the sealing position into the connecting position against the spring action, enabling the first duct to be passed through the duct bore.

According to a further elaboration of the invention, the sealing element comprises a recess intended for creating, in the connecting position of the sealing element, the fluid connection between the two duct bore parts. With a thus designed sealing element, it is possible that both end faces thereof extend outside the receiving part of the device, enabling the control means to control the sealing element from the two end faces.

According to a further elaboration of the invention, the sealing element has a contact area abutting against the first duct under spring action, the orientation of the sealing element and the shape of the recess being designed so that the contact area is line-shaped or point-shaped. Such line-shaped or point-shaped contact area results in a better and firmer clamping of the first duct, because of the so-called slanting effect.

By means of the device according to the invention, all above-described problems of the known gas chromatograph can be solved. To this end, the invention provides an injector of a gas chromatograph provided with a needle-insert part comprising the device according to the invention.

The invention moreover provides a coupling device for a capillary gas chromatography column, which coupling device comprises the device according to the invention and which coupling device may form a part of the outlet part of an injector and the inlet part of a detector of a gas chromatograph. Due to the fact that the coupling of the gas chromatography column by means of the coupling devices according to the invention has become particularly simple, it now also becomes possible to accommodate the gas chromatography column in a cassette which can be placed in a very simple manner without the risk of damage to the capillary gas chromatography column and without necessitating trained analysts. Obviously, the invention also relates to such cassette and to a gas chromatograph provided with an injector and/or a detector according to the invention, or with directing means adapted for cooperation with a cassette according to the invention.

Further elaborations of the invention are described in the subclaims and will be specified on the basis of a number of exemplary embodiments, with reference to the accompanying drawings. In these drawings:

FIGS. 10a–10d show the different stages of coupling a gas chromatography column end to a coupling device according to the invention.

Figure 1:
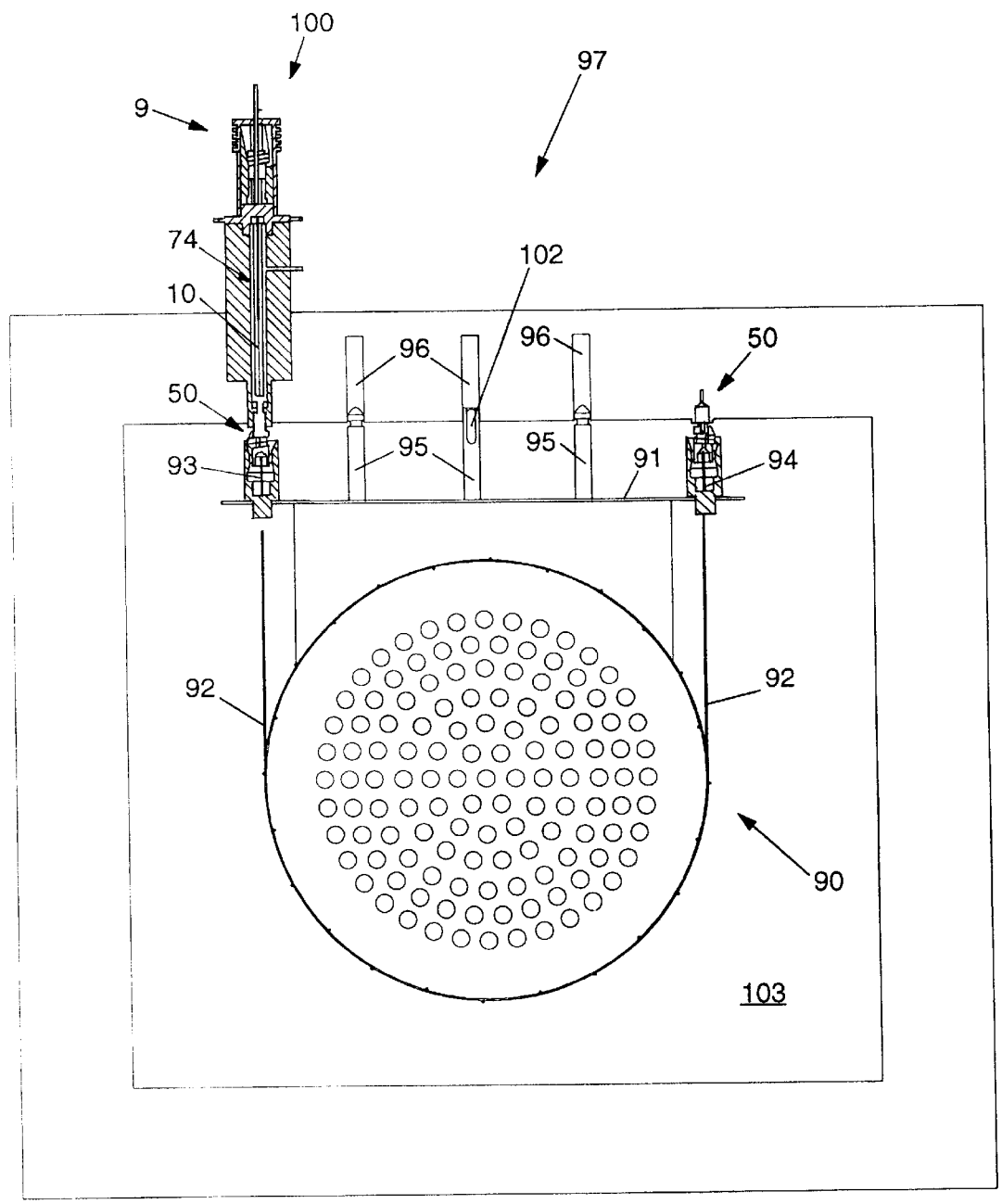
FIG. 1 is a sectional view of a first embodiment of a gas chromatograph.

FIG. 1 shows a gas chromatograph 97 comprising an oven space 103 in which a capillary gas chromatography column 92 is located. In the drawing, the gas chromatograph 97 is on the left-hand side provided with an injector 100 comprising a needle-insert part 9, an injector chamber 10 and an outlet part 50, to which outlet part 50 the feed end 93 of the capillary column 92 can be coupled. The gas chromatograph also comprises a detector of which only the inlet end 50 is shown. The inlet end 50 of the detector is adapted to be connected to the discharge end 94 of the capillary column 92. In the present case, the capillary column 92 forms part of a cassette 90 having a housing 91 and directing means 95 that are adapted to cooperate with directing means 96 in the wall of the oven of gas chromatograph 97.

Presently, now that the global construction of an exemplary embodiment of the gas chromatograph is known, the different parts thereof will be discussed in detail.

Figure 3:
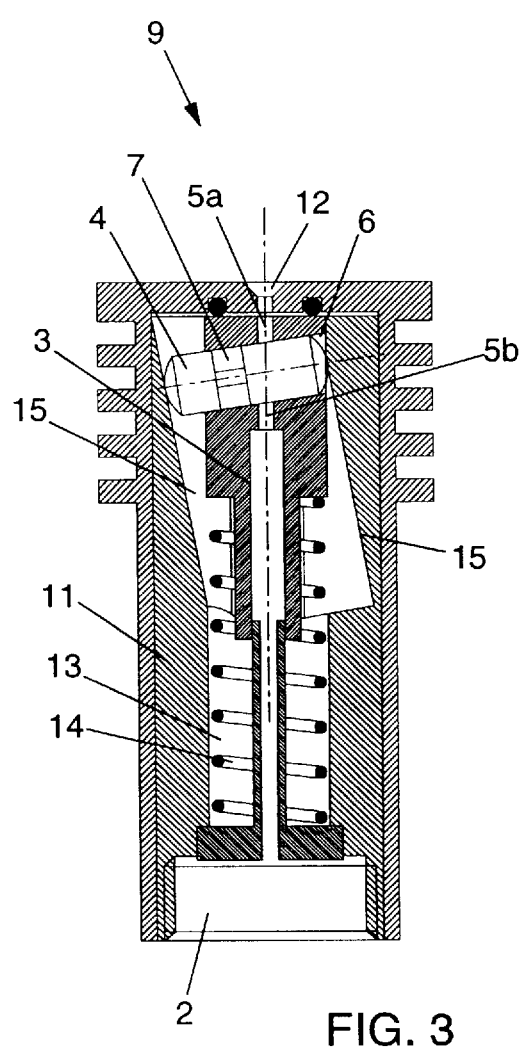
FIGS. 3 and 4 are sectional views of a needle-insert part of an injector of a gas chromatograph.
Figure 4:
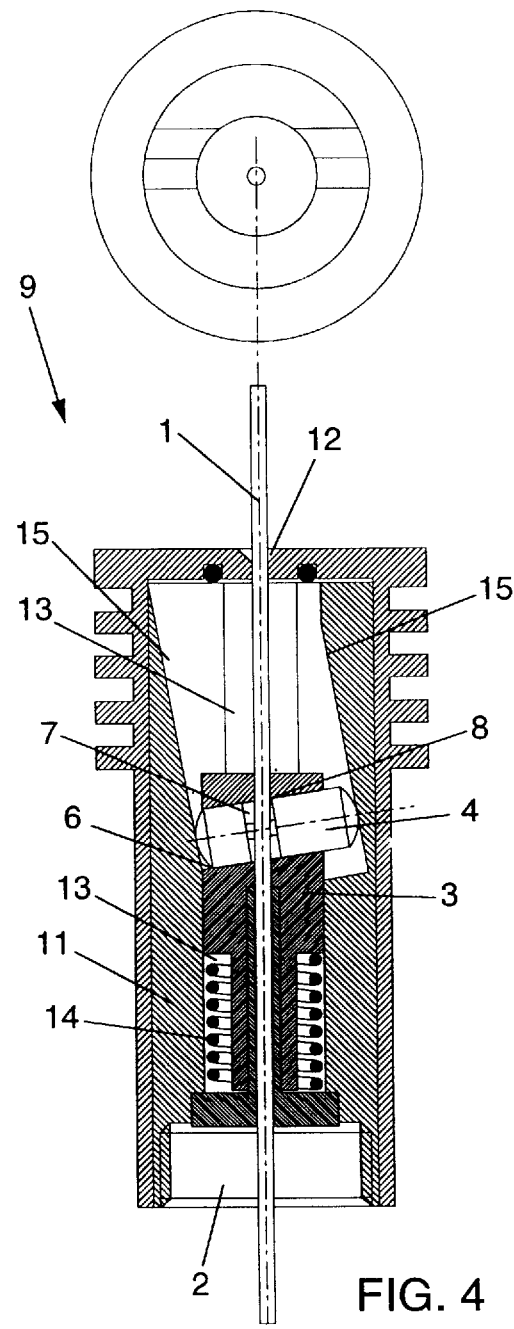

FIG. 3 shows an exemplary embodiment of a needle-insert part 9 of an injector according to the invention. The needle-insert part comprises a receiving part 3 and a sealing element 4. The receiving part 3 is provided with a duct bore 5 in which the needle 1 is slidably receivable. The receiving part 3 also comprises a sealing element bore 6 which intersects the duct bore 5 and in which the sealing element 4 is slidably accommodated. The sealing element 4 is provided with a recess 7. The sealing element 4 is adapted to assume a sealing position in which the duct bore 5 is sealed and to assume a connecting position in which the two duct bore parts 5a, 5b on either side of the sealing element bore 6 are in fluid connection with each other via the recess 7. By means of a spring 14, the sealing element 4 is biased in the sealing position under spring action. By a line-shaped contact area 8, the sealing element 4 abuts against the needle 1 when it is located in the duct bore 5. In this manner, the needle is clamped in the duct bore, so that it can extend by its free end into the injector chamber 2 or 10. The needle-insert part 9 further comprises a housing 11, a needle access opening 12 and a housing bore 13. The needle access opening 12 opens into the housing bore 13. As already pointed out hereinabove, the duct bore 5 in the receiving part 3 can constitute a passage between the needle access opening 12 and the injector chamber 10 which is connected, via the connection 2, to the needle-insert part 9. The receiving part 3 is slidably accommodated in the housing bore 13 and is pressed by spring pressure of the spring 14 under bias, into a first, in this case upper position. The housing bore 13 further comprises a guide section 15 cooperating with the sealing element 4. By passing the needle 1 through the needle access opening 12 and pressing it downwards, the receiving part 3 is brought into a second position, against the spring pressure. The guide section 15 is designed so that in this second position of the receiving part 3, the sealing element 4 is in the connecting position. In this connecting position, shown in FIG. 4, the needle 1 extends through the duct bore 5 and into the injector chamber 10. The spring 14 presses the receiving part 3 upwards; however, because of the presence of the needle 1 in the duct bore 5, the receiving part 3 cannot move upwards. Only when the needle 1 is pulled out of the duct bore 5, can the sealing element 4 move freely leftwards again, whereby the receiving part will be pressed upwards and the duct bore 5 is directly sealed. The sealing of the duct bore 5 is of great importance, because the entry of air into the injector chamber 10 must absolutely be avoided, as this would destroy the measuring values. The needle-insert part shown is highly user-friendly and does not cause any danger of disturbing the measurement in the manner as is actually possible with a needle-insert part of an injector comprising a septum which is made of rubber or plastic and through which the needle is to be passed. Moreover, the insertion of the needle 1 can be carried out by an untrained operator.

Figure 5:
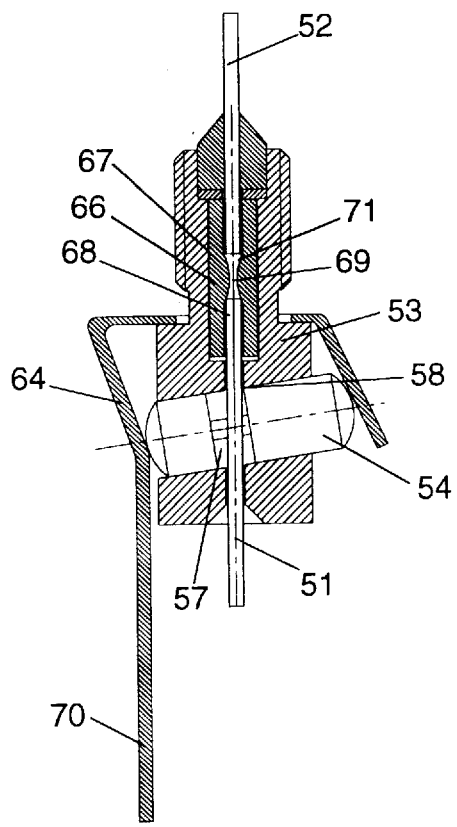
FIGS. 5 and 6 show a first exemplary embodiment of a coupling device for a gas chromatography column for an injector or detector.
Figure 5:
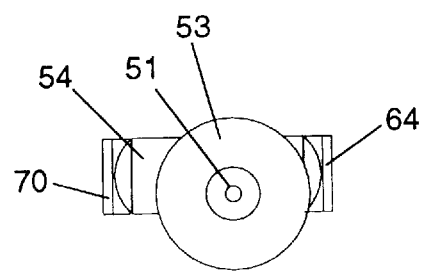
Figure 6:
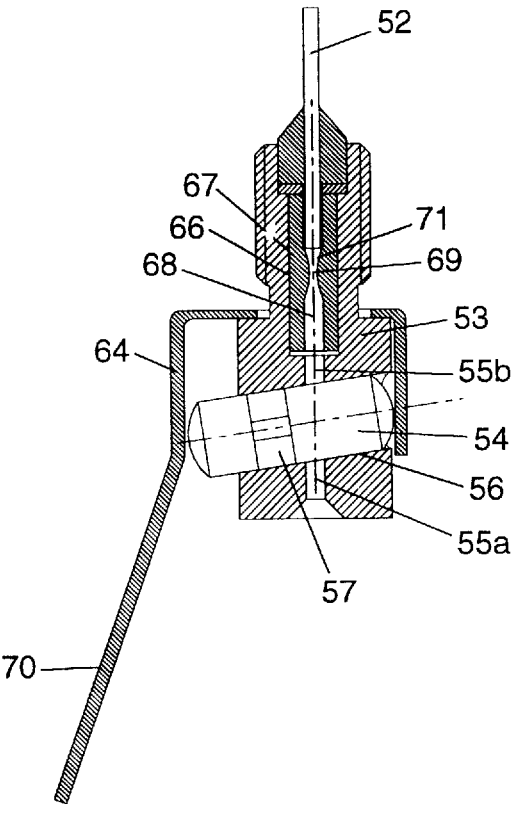
Figure 6:
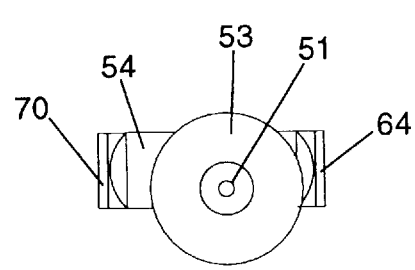

FIGS. 5 and 6 show a coupling device 50 for a capillary gas chromatography column 51. This coupling device 50, too, comprises the device according to the invention. After all, the coupling device comprises a receiving part 53 and a sealing element 54. The receiving part 53 is provided with a duct bore 55 in which the capillary column 51 is slidably receivable. The receiving part 53 is also provided with a sealing element bore 56 which intersects the duct bore 55 and in which the sealing element 54 is slidably accommodated. The sealing element 54 is provided with a recess 57 and is adapted to assume a sealing position in which the duct bore 55 is sealed and a connecting position in which the two duct bore parts 55a, 55b on both sides of the sealing element bore 56 are in fluid connection with each other, via the recess 57. The sealing element 54 is biased in the sealing position by a spring 64 under spring action. The connecting position is shown in FIG. 5 and the sealing position is shown in FIG. 6. FIGS. 5 and 6 both shown a sectional view as well as a bottom view of the coupling device. In the exemplary embodiment shown, the duct bore 55 in the receiving part 53 is provided with a chamber 66 in which a column-connecting piece 67 is accommodated having a column-receiving bore 68 in which the capillary gas chromatography column 51 is receivable. The column-receiving bore converges conically, viewed from the sealing element 54. This conical constriction 69 has an inside diameter which, at least at the narrowest portion of the constriction 69, is smaller than the outside diameter of the capillary gas chromatography column 51. Preferably, the angle which the wall of the constriction 69 includes with the center line of the column-receiving bore 68 is selected so that the gas chromatography column 51 is receivable in the constriction 69 in a withdrawable manner. Moreover, according to a further elaboration of the invention, the column-connecting piece 67 is preferably manufactured from glass. With such a column-connecting piece 67 having a conical constriction 69, a gastight coupling between an end of a capillary gas chromatography column 51 and the column-connecting piece 67 is possible. The external coating of the gas chromatography column 51 flows slightly when the column 51 is pressed on in the constriction 69, which flow brings about a hermetic sealing. The coupling as described can serve both as outlet part of an injector 100 and as inlet part of a detector 200.

In an injector according to the prior art, it is particularly important that the feed end of the gas chromatography column extends by the correct length into the injector chamber 10. If this length is not correct, the measurements will be influenced thereby. Consequently, placing a known gas chromatography column in the outlet part of a known injector can only be performed by trained analysts. This problem can be solved in a simple manner with the injector according to the invention, comprising a coupling device according to the invention. To this end, according to a further elaboration of the invention, the injector is characterized in that the column-receiving bore 68 of the column-connecting piece 67 diverges conically from the constriction 69, viewed from the sealing element 54, with a second duct 52 being fixedly accommodated in the enlargement 71. The second duct 52 preferably has the same inside and outside diameter as in the case of a capillary gas chromatography column and has a fixed, standardized length whereby this second duct extends into the injector chamber 10. As the second duct 52 is fixedly connected to the coupling device 50 and is not removed when the capillary gas chromatography column 51 is being removed, it is guaranteed that the measurements of the gas chromatograph are in any case not disturbed on account of the gas chromatography column not being located at the correct depth in the injector chamber 10.

Figure 7:
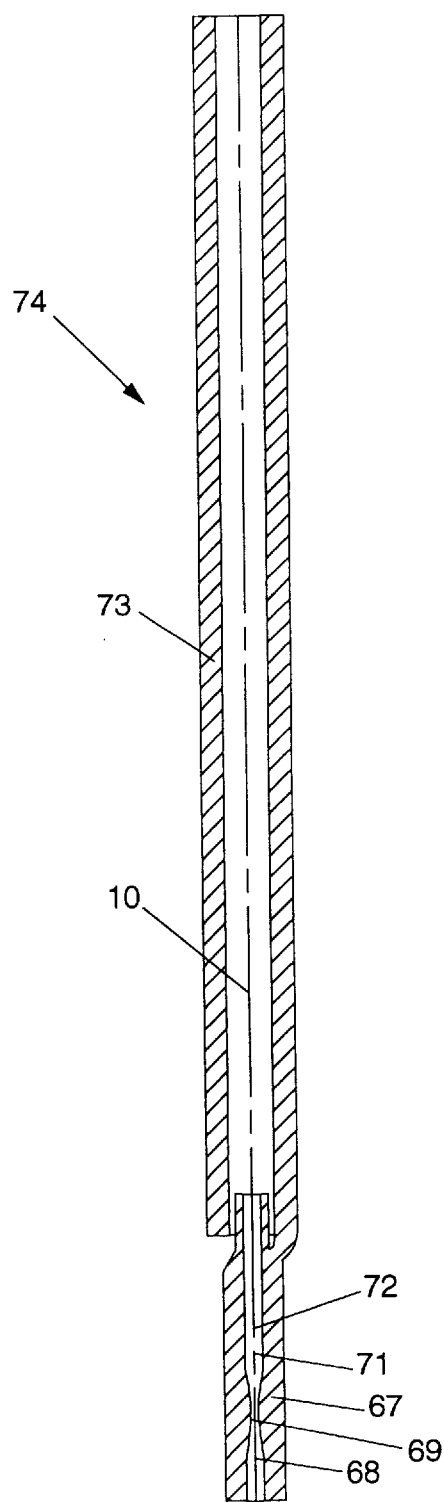
FIG. 7 shows a part of an injector of a gas chromatograph, which part comprises the injector chamber.
Figure 7:

According to an alternative further elaboration of the injector according to the invention, this injector is characterized in that, viewed from the sealing element 54, the column-receiving bore 68 of the column-connecting piece 67 diverges conically from the constriction 69 and blends with a second duct 72, which second duct 72 has a standardized, fixed length and extends into the injector chamber 10. The injector chamber 10 is bounded by a sleeve 73 made of glass. The column-connecting piece 67 and the second duct 72 are likewise manufactured from glass. According to this alternative further elaboration, the column-connecting piece 67, the second duct 72, and a sleeve 73 comprising the injector chamber 10 are an integral part of one-piece design. This part is shown in sectional view and in bottom view in FIG. 7 and can take the place of the column-connecting piece 67 and the associated second duct 52 from FIGS. 5 and 6.

When the capillary gas chromatography column 51 is to be connected to the coupling device 50, the operator presses against the lever 70 which is connected to the spring 64, causing the sealing element 54 to be pressed into the connecting position. Next, the column end 51 can be inserted into the coupling device 50, so that the end thereof engages the constriction 69, after which the lever 70 can be released and the column 51 is fixed under the influence of the friction between the duct bore 55 and the column end 51. In this manner, a very simple assembly of the gas chromatography column 51 is obtained.

Figure 2:
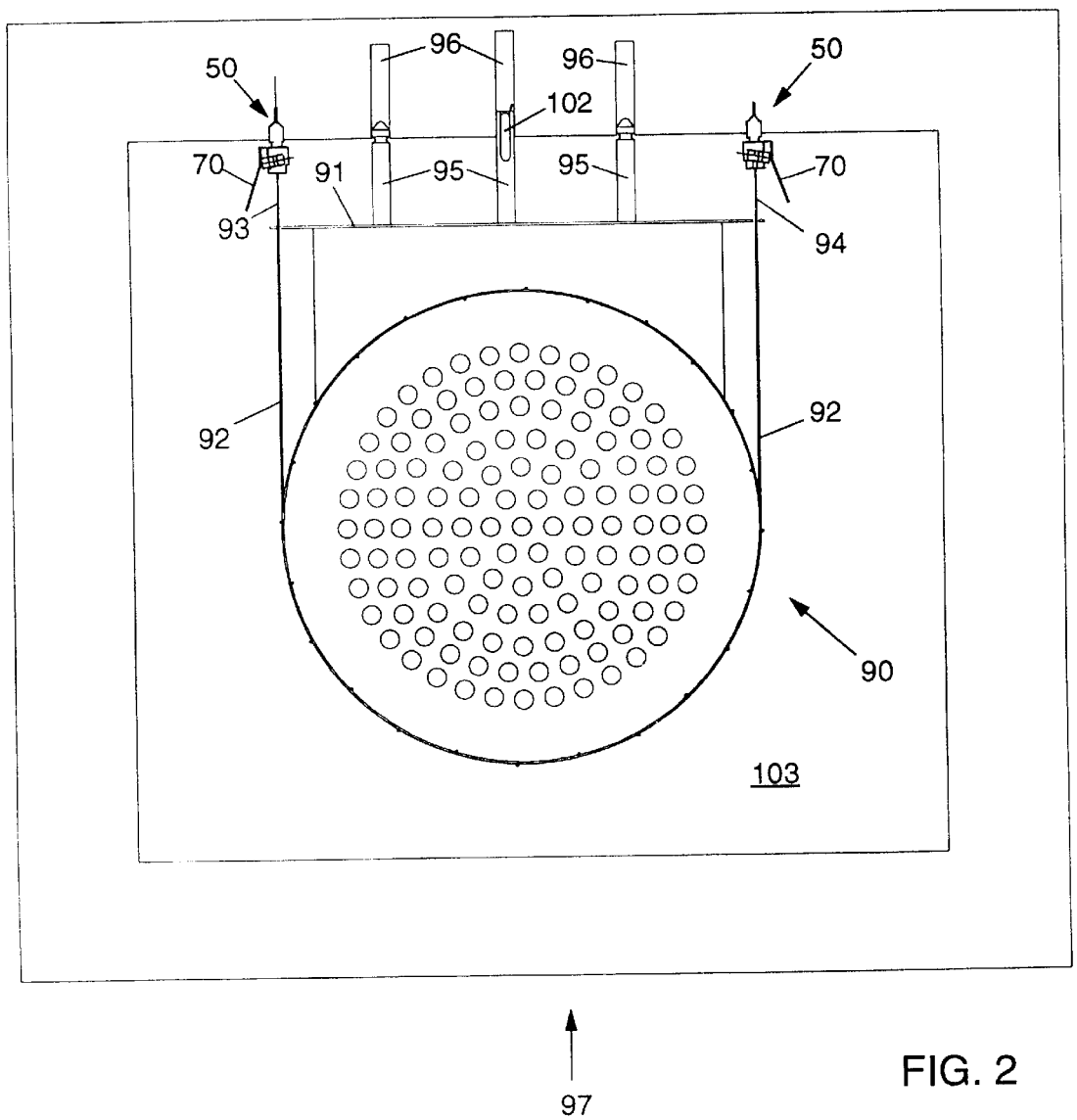
FIG. 2 is a sectional view of a second embodiment of a gas chromatograph.

As has already been observed hereinabove, both the outlet part of the injector and the inlet part of the detector may be provided with such coupling device. A gas chromatograph 97 where this is the case is shown in FIG. 2. In FIG. 2, the capillary gas chromatography column is designated by reference numeral 92, the feed end is designated by reference numeral 93 and the discharge end is designated by reference numeral 94. For clarity's sake, the other parts of the injector and the detector are not shown in FIG. 2. However, it is understood that the gas chromatography column is accommodated in a cassette comprising a housing 91 and directing means 95. The directing means 95 are intended for cooperation with directing means 96 in the housing of the gas chromatograph 97.

In some cases, the detector may also be a mass spectrograph. The detection chamber of a mass spectrograph typically contains an inert gas or rinsing gas under low pressure. In the presently known gas chromatographs of which the detector is connected to a mass spectrograph, the changing of the capillary gas chromatography column results in that the detection chamber of the mass spectrograph fills up with ambient air. Therefore, before the next measurement can be started, the detection chamber of the mass spectrograph should, after the changing of the column, be rinsed with rinsing gas for a number of hours in order to effectively remove the ambient air therefrom. This rinsing operation takes about three hours, in which period no measurements can be conducted.

Figure 8:
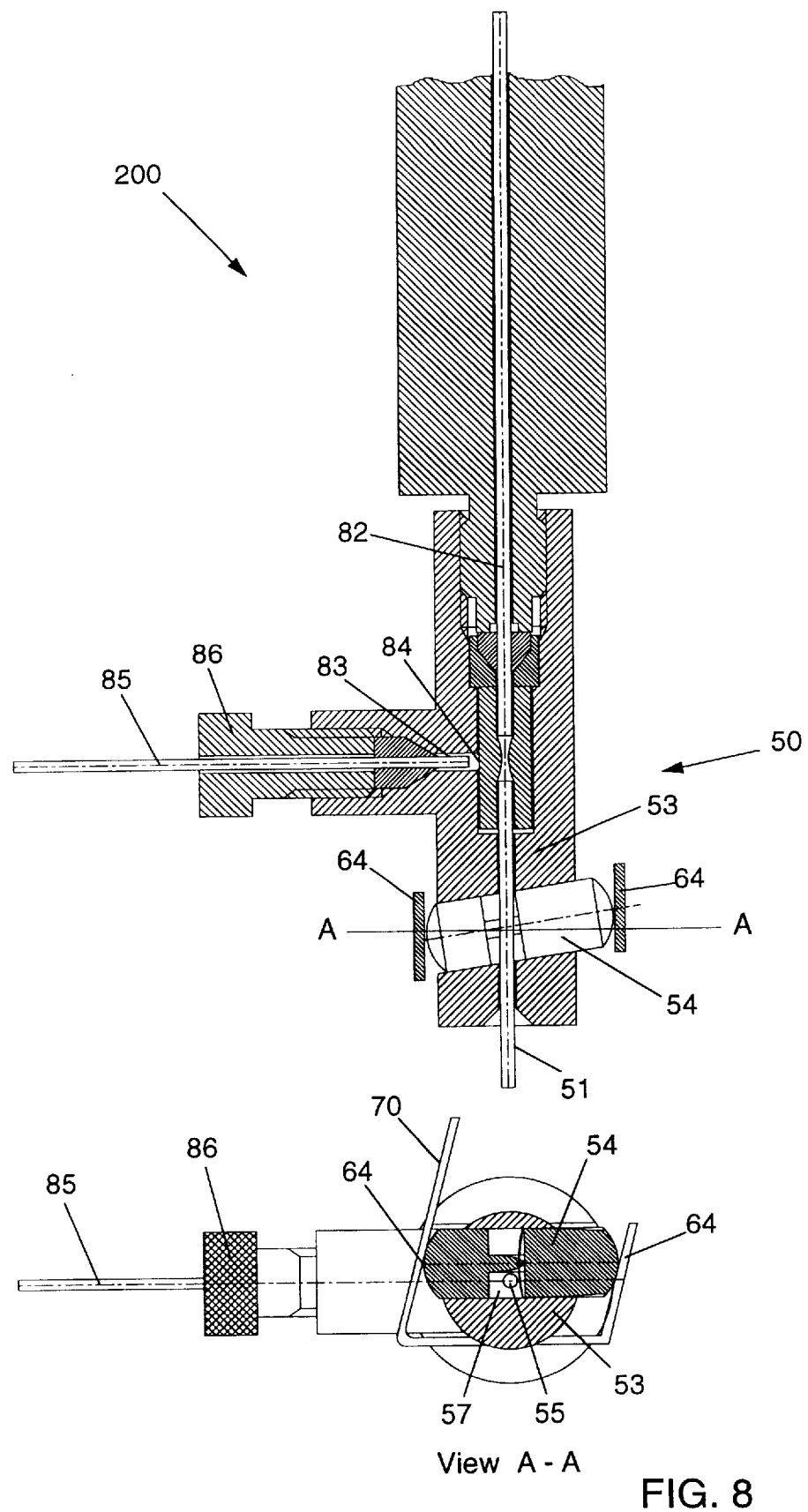
FIGS. 8 and 9 show an exemplary embodiment of a coupling part for a capillary gas chromatography column for a detector connected to a mass spectrograph.
Figure 9:
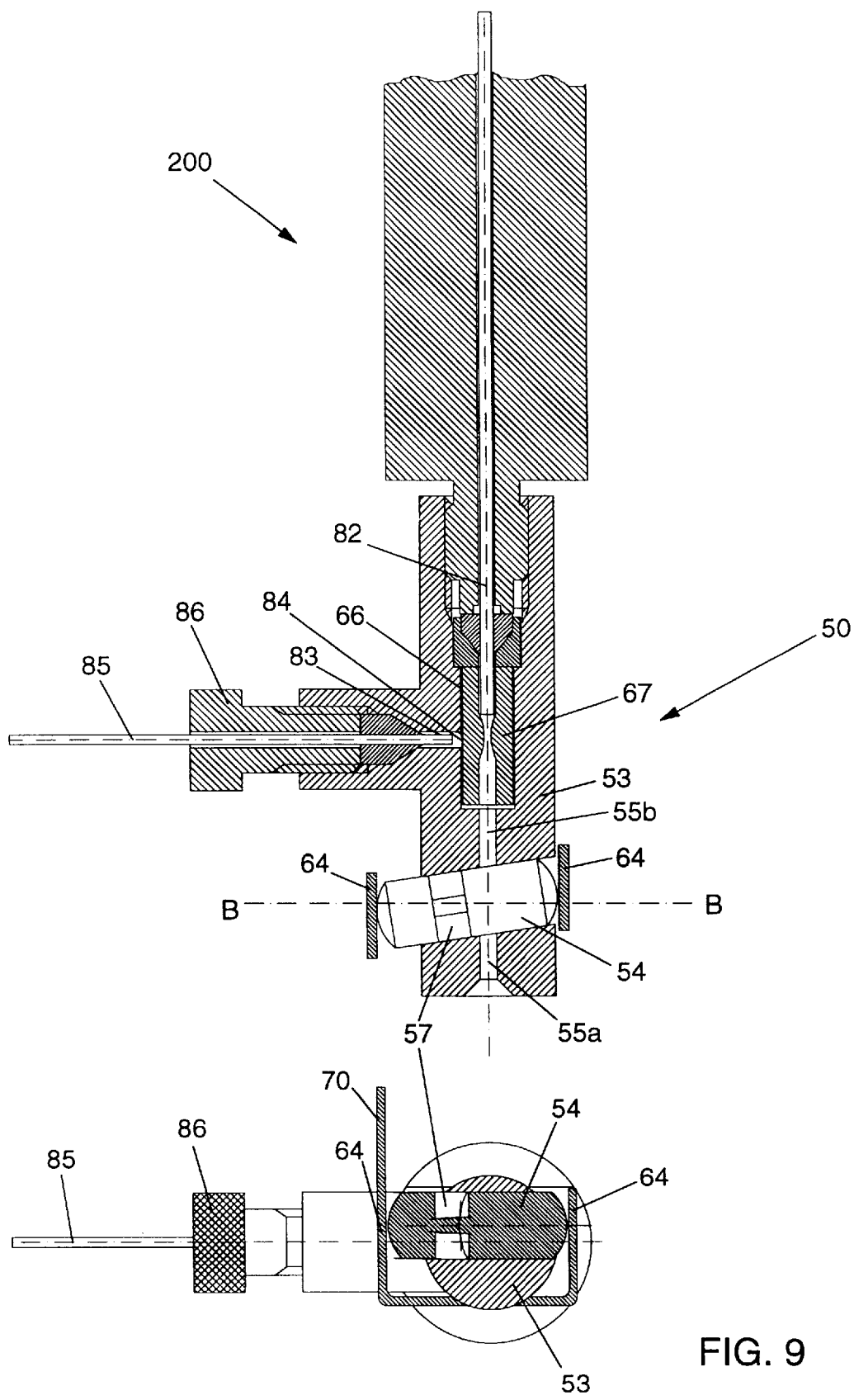

To solve this problem, the coupling device 50, forming the inlet part of a detector 200, which detector 200 is connected to a mass spectrograph, is characterized in that the receiving part 53 is provided with a rinsing-gas bore 83 with opens into a rinsing-gas feed opening 84 in the duct bore 55 in the receiving part 53. The ringing-gas feed opening 84 is located between the sealing element 54 and the second duct 82. Such detector is shown in FIGS. 8 and 9. When the gas chromatography column 51 is being uncoupled, the sealing element 54 slips from the position shown in FIG. 8 into the position shown in FIG. 9, under the influence of the spring 64. This prevents ambient air from flowing to the mass spectrograph via the duct bore 55 and the second duct 82. To prevent leak-off air from flowing to the mass spectrograph, rinsing gas is passed via the rinsing-gas bore 83 and rinsing-gas feed opening 84 to the duct bore 55. By means of a clamp fitting 86, a rinsing-gas feed duct 85 is connected to the rinsing-gas bore 83. It is thus effected that after the removal of a capillary gas chromatography column and the placing of another capillary gas chromatography column, new measurements can directly be started, so that a much better occupation of the gas chromatograph is realized.

As the coupling of the gas chromatography column 92 to the coupling devices 50 of the injector and the detector respectively has become much simpler, according to a further elaboration of the invention, there is also provided the possibility of accommodating the capillary gas chromatography column in a cassette 90 which can be inserted into the gas chromatograph by an operator who has had much less training than an analyst. Such cassette 90 is provided with a housing 91 and a capillary gas chromatography column 92 having a feed end 93 and a discharge end 94. The cassette 90 moreover comprises directing means 95 adapted for cooperation with directing means 96 that are provided in a gas chromatograph 97 into which the cassette 90 can be inserted. Such gas chromatograph 97 with cassette 90 is shown in FIGS. 1 and 2. In the gas chromatograph shown in FIG. 2, the feed end 93 and the discharge end 94 project from the housing 91 in such a manner that they can cooperate with the coupling device 50 as shown in FIGS. 5 and 6.

A somewhat more user-friendly type of cassette 90 is shown in FIG. 1. Here, the feed end 93 and the discharge end 94 of the gas chromatography column 92 are each received in a protective recess 98, 99. The protective recess 98 surrounding the feed end 93 is adapted for cooperation with an injector 100 as shown in FIG. 1, of which the coupling device 50 is shown in FIGS. 10A–10D. FIGS. 10A–10D show the coupling operation between the feed end 93 of a gas chromatography column 92 and the coupling device 50 of the injector 100. The protective recess 99 surrounding the discharge end 94 is adapted for cooperation with a detector 200 which comprises a coupling device 50 similar to that of the injector. Hence, FIGS. 10A–10D can as well be considered a representation of the coupling operation between the discharge end 94 of the gas chromatography column and the inlet part 50 of a detector 200. As the feed end 93 and the discharge end 94 of the capillary gas chromatography column are located in the protective recess 98 and 99 respectively, damage to these ends 93, 94 is virtually excluded. According to a further elaboration of the cassette 90 of the invention, each protective recess 98, 99 is provided with an internal section 101 adapted to cooperate, during the insertion of the cassette 90, with the sealing element 54 in such a manner that during the path travelled by the protective recess 98, 99 relative to the coupling device 50 when the cassette 90 is being inserted, the sealing element 54 is moved from the sealing position into the connecting position against spring action, and is subsequently released again when both the feed end 93 and the discharge end 94 of the capillary gas chromatography column 92 have been received in the column-connecting piece 67. In this manner, even the operation of the sealing element 54 is automized through the presence of the section 101, so that the operator merely has to snap the cassette 90 in position, after which a connection has been established. The different stages of establishing the connection are shown in FIGS. 10A–10D.

As is clearly shown in FIGS. 1 and 2, the cassette may be provided with a transponder 102 or a like electronic chip which contains data about the gas chromatography column 92 and is optionally provided with a memory for storing data. Obviously, the associated gas chromatograph for such cassette 90 should be provided with electronic reading and/or writing means for respectively reading out or filling the memory of the transponder 102 or a like electronic chip.

To prevent damage to the feed end 93 and the discharge end 94 of the gas chromatography column 92 during insertion of the cassette 90, it is particularly favorable when these ends 93, 94 are resiliently connected to the cassette housing 91, to permit some movement of both the feed end 93 and the discharge end 94 relative to the housing 91. FIG. 10 clearly shows that the feed end 93 and the discharge end 94 respectively are connected to the housing 91 via a spring 104, to obtain the above-mentioned freedom of movement of the feed end 93 and the discharge end 94 respectively. The coupling device 50 of the injector and the detector respectively has its bottom side provided with a conical centering recess 105, so that the feed end 93 and the discharge end 94 respectively of the gas chromatography column 92 are guided to the duct bore 55.

It is understood that the invention also relates to a gas chromatograph comprising an injector with a needle-insert part according to claim 3 or to a gas chromatograph comprising an injector according to any one of claims 7–9 and/or a detector according to any one of claims 10–12. Obviously, the protection also covers a gas chromatograph comprising directing means 96 adapted for cooperation with a cassette 90 according to any one of claims 13–15. A gas chromatograph having electronic reading and/or writing means for reading out, respectively filling the memory of the transponder 102 or like electronic chip of the cassette 90 according to claim 16 also belongs to the inventive concept.

It is understood that the exemplary embodiments described are given by way of example only, and that various modifications are possible within the framework of the invention.

We claim:

1. Device for connecting a first duct (1, 51) of a very small diameter, such as for instance a needle (1) or a capillary column (51), to a second duct of a gas chromatograph (2, 52, 72, 82), wherein the device comprises a receiving part (3, 72, 82) and a sealing element (4, 54), wherein the receiving part (3, 53) is provided with a duct bore (5, 55) in which the first duct (1, 51) is slidably receivable, wherein the receiving part (3, 53) is also provided with a sealing-element bore (6, 56)

which intersects the duct bore (5, 55) and in which the sealing element (4, 54) is slidably received, wherein the sealing element (4, 54) is adapted to assume a sealing position in which the duct bore (5, 55) is sealed and is adapted to assume a connecting position in which the two duct bore parts (5a, 5b, 55a, 55b) on either side of the sealing-element bore (6, 56) are in fluid connection with each other, wherein the sealing element (4, 54) is biased in the sealing position by a spring (14, 64) under spring action, characterized in that the device comprises control means (15; 64, 70; 101) which engage the sealing element (4, 54) for bringing the sealing element (4, 54) from the sealing position into the connecting position, against the spring action.

2. A device according to claim 1, characterized in that the sealing element (4, 54) comprises two opposite end faces, wherein the control means are designed as a guide section (15, 101) engaging at least one of the end faces of the sealing element (4, 54).

3. A device according to claim 1, characterized in that the sealing element (4, 54) comprises two opposite end faces, wherein the control means are designed as a leaf-spring element (64) comprising a lever (70) by means of which the position of the leaf spring (64) and, accordingly, the position of the sealing element (4, 54) is adjustable.

4. A device according to claim 1, characterized in that the sealing element (4, 54) comprises a recess (7, 57) intended for creating, in the connecting position of the sealing element, the fluid connection between the two duct bore parts (5a, 5b, 55a, 55b).

5. A device according to claim 1, characterized in that in the connecting position, the sealing element (4, 54) has a contact area (8, 58) abutting against the first duct (1, 51) under spring action, wherein the orientation of the sealing element (4, 54) and the shape of the recess (7, 57) are designed so that the contact area (8, 58) is line-shaped or point-shaped.

6. An injector (100) of a gas chromatograph comprising a needle-insert part (9) comprising a device according to claim 1, wherein the injector comprises an injector chamber (10), wherein the needle-insert part (9) comprises a housing (11), a needle access opening (12), a housing bore (13) and a spring (14), wherein the needle access opening (12) opens into the housing bore (13), wherein the duct bore (5) in the receiving part (3) can form a passage between the needle access opening (12) and the injector chamber (10) forming the second duct (2), wherein the receiving part (3) is slidably accommodated in the housing bore (13) and is pressed into a first position by spring pressure of the spring (14) under bias, wherein the housing bore (13) is provided with a guide section (15) which serves as control means and cooperates with the sealing element (4), wherein the receiving part (3) can be moved into a second position against the spring pressure, wherein the guide section (15) is designed so that in the first position of the receiving part (3), the sealing element (4) is in the sealing position and that in the second position of the receiving part (3), the sealing element (4) is in the connecting position.

7. A coupling device (50) for a capillary gas chromatography column (51), wherein the coupling device (50) is the device according to claim 1, wherein the duct bore (55) in the receiving part (53) is provided with a chamber (66) accommodating a column-connecting piece (67) provided with a column-receiving bore (68) in which the capillary gas chromatography column (51) is receivable, said column-receiving bore (68) converging conically, viewed from the sealing element (54), said conical constriction (69) having an inside diameter which at least at the narrowest portion of the constriction (69) is smaller than the outside diameter of the capillary gas chromatography column (51).

8. A coupling device according to claim 7, characterized in that the angle which the wall of the constriction (69) includes with the center line of the column-receiving bore (68) is selected so that the gas chromatography column (51) is receivable in the constriction (69) in a withdrawable manner.

9. A coupling device according to claim 7, characterized in that the column-connecting piece (67) is manufactured from glass.

10. An injector (100) of a gas chromatograph, said injector comprising an outlet part (50) and an injector chamber (10), wherein the outlet part (50) of the injector (100) comprises a coupling device (50) according to claim 7.

11. An injector according to claim 10, wherein the column-receiving bore (68) of the column-connecting piece (67) diverges conically from the constriction (69), viewed from the sealing element (54), wherein the second duct (52) is fixedly accommodated in the enlargement (71), said second duct (52) having a standardized fixed length and extending into the injector chamber (10).

12. An injector according to claim 10, wherein the column-receiving bore (68) of the column-connecting piece (67) diverges conically from the constriction (69), viewed from the sealing element (54), and blends with the second duct (72), said second duct (72) having a standardized fixed length and extending into the injector chamber (10), wherein the injector chamber (10) is bounded by a sleeve (73) made of glass, wherein the column-connecting piece (67) and the second duct (72) are likewise manufactured from glass, wherein the column-connecting piece (67), the second duct (72) and a sleeve (73) comprising the injector chamber (10) form an integral, one-piece part.

13. A detector (200) of a gas chromatograph, said detector (200) comprising an inlet part (50) and a detection chamber, wherein the inlet part (50) of the detector (200) comprises a coupling device (50) according to claim 7.

14. A detector (200) according to claim 13, wherein the column-receiving bore (68) of the column-connecting piece (67) diverges conically from the constriction (69), viewed from the sealing element (54), wherein the second duct (52, 82) is fixedly accommodated in the enlargement (71), said second duct (52, 82) leading to the detection chamber.

15. A detector according to claim 13, characterized in that the second duct (82) leads to a detection chamber of a mass spectrograph, wherein the receiving part (53) is provided with a rinsing-gas bore (83) which opens into a rinsing-gas feed opening (84) in the duct bore (55) in the receiving part (53), wherein the rinsing-gas feed opening (84) is located between the sealing element (54) and the second duct (82).

16. A gas chromatograph comprising an injector according to claim 6.

* * * * *

UNITED STATES PATENT AND TRADEMARK OFFICE
CERTIFICATE OF CORRECTION

PATENT NO. : 5,889,197
DATED : March 30, 1999
INVENTOR(S) : Martinus Frans van der Maas, et al.

It is certified that error appears in the above-identified patent and that said Letters Patent is hereby corrected as shown below:

Title page,
Item [75], Inventors,
"Arnumuiden", should read -- Arnemuiden --;

Item [73], Assignee,
"Explotaitie", should read -- Exploitatie --;
"Middleburg", should read -- Middelburg --;

Item [21], Appl. No.
"967,676", should read -- 08/967,676 --; and

Attorney,
"Wiengarten", should read -- Weingarten --.

Signed and Sealed this

Sixth Day of November, 2001

Attest:

NICHOLAS P. GODICI
Attesting Officer
Acting Director of the United States Patent and Trademark Office